United States Patent
Geistlich et al.

(10) Patent No.: US 7,208,177 B2
(45) Date of Patent: *Apr. 24, 2007

(54) RESORBABLE EXTRACELLULAR MATRIX FOR RECONSTRUCTION OF CARTILAGE

(75) Inventors: Peter Geistlich, Stansstad (CH); Lothar Schloesser, Darmstadt (DE)

(73) Assignee: Ed. Geistlich Soehne AG fuer Chemische Industrie, Wolhusen (CH)

( * ) Notice: Subject to any disclaimer, the term of this patent is extended or adjusted under 35 U.S.C. 154(b) by 761 days.

This patent is subject to a terminal disclaimer.

(21) Appl. No.: 09/988,805

(22) Filed: Nov. 20, 2001

(65) Prior Publication Data

US 2002/0090391 A1 Jul. 11, 2002

Related U.S. Application Data

(63) Continuation-in-part of application No. 09/986,757, filed on Nov. 9, 2001, now Pat. No. 6,676,969, which is a continuation of application No. 08/894,517, filed as application No. PCT/GB96/00399 on Feb. 22, 1996, now Pat. No. 6,326,029.

(30) Foreign Application Priority Data

Feb. 22, 1995 (GB) .................................. 9503492.2

(51) Int. Cl.
  *A61K 9/10* (2006.01)
  *A61K 47/42* (2006.01)

(52) U.S. Cl. ...................................... 424/484; 424/428
(58) Field of Classification Search ................ 424/484, 424/422–423, 426, 548; 514/944; 530/356, 530/442, 422, 425–427, 840
See application file for complete search history.

(56) References Cited

U.S. PATENT DOCUMENTS 5,162,430 A    11/1992   Rhee et al.

(Continued)

FOREIGN PATENT DOCUMENTS

AU         660045 B    3/1993

(Continued)

OTHER PUBLICATIONS

H.A. Breinan et al., "Reparative Tissues in Articular Cartilage Defects in a Canne Model Treated by Microfracture", 45th Annual Meeting, Orthopaedic Research Society, Feb. 1-4, 1999, Anaheim, CA. (one page ).

(Continued)

*Primary Examiner*—Sharon E. Kennedy
(74) *Attorney, Agent, or Firm*—Rothwell, Figg, Ernst & Manbeck, PC

(57) ABSTRACT

A resorbable extracellular matrix for reconstruction of cartilage tissue includes a purified collagen II derived from natural cartilage tissue from which non-collagen proteins have been removed. The matrix can be utilized as a scaffold implant for meniscal or vertebral cartilage regeneration.

11 Claims, 1 Drawing Sheet

U.S. PATENT DOCUMENTS

| | | | |
|---|---|---|---|
| 5,167,961 | A | 12/1992 | Lussi et al. |
| 5,206,023 | A | 4/1993 | Hunziker |
| 5,306,311 | A * | 4/1994 | Stone et al. ............. 623/14.12 |
| 5,413,597 | A | 5/1995 | Krajicek |
| 5,417,975 | A | 5/1995 | Lussi et al. |
| 5,523,348 | A | 6/1996 | Rhee et al. |
| 5,541,295 | A | 7/1996 | Barrach et al. |
| 5,567,806 | A | 10/1996 | Abdul-Malak et al. |
| 5,573,771 | A | 11/1996 | Geistlich et al. |
| 5,624,463 | A | 4/1997 | Stone et al. |
| 5,759,190 | A | 6/1998 | Vibe-Hansen et al. |
| 5,837,278 | A | 11/1998 | Geistlich et al. |
| 5,842,477 | A * | 12/1998 | Naughton et al. .......... 128/898 |
| 6,153,292 | A | 11/2000 | Bell et al. |
| 6,221,109 | B1 | 4/2001 | Geistlich et al. |
| 6,352,558 | B1 | 3/2002 | Spector |
| 6,676,969 | B2 * | 1/2004 | Geistlich et al. ............. 424/484 |

FOREIGN PATENT DOCUMENTS

| | | |
|---|---|---|
| AU | 663150 B | 6/1993 |
| DE | 19654884 A1 | 9/1997 |
| FR | 2679778 A1 | 2/1993 |
| WO | WO 9005755 A1 | 5/1990 |
| WO | WO 9013302 A1 | 11/1990 |
| WO | WO 9213565 A1 | 8/1992 |
| WO | WO 93/11723 * | 6/1993 |
| WO | WO 9310722 A2 | 6/1993 |
| WO | WO 9311723 A1 | 6/1993 |
| WO | WO 9319168 A1 | 9/1993 |
| WO | WO 9518638 A1 | 7/1995 |
| WO | WO 9624310 A1 | 8/1996 |
| WO | WO 9625961 A1 | 8/1996 |
| WO | WO 9732616 A1 | 9/1997 |
| WO | WO 9802976 A1 | 1/1998 |
| WO | WO 9919005 A1 | 4/1999 |

OTHER PUBLICATIONS

C.R. Lee et al., "Harvest and Selected Cartilage Repair Procedures Affect Mechanical and Biochemical Properties of Uninvolved Articular Cartilage in the Canine Knee", 45th Annual Meeting, Orthopaedic Research Society, Feb. 1-4, 1999, Anaheim, CA. (one page).

C.R. Lee et al., "The Contractile Behavior of Articular Chondrocytes in Collagen Matrices In Vitro", Tissue Engineering Soc., Dec. 4-6, 1998, Orlando, Fla. (one page).

S.M. Mueller et al., "Alpha-Smooth Muscle Actin in Bovine Meniscus Cells Seeded in Type I and Type II Collagen-Gag Matrices", 44th Annual Meeting, Orthopaedic Research Society, Mar. 16-19, 1998, New Orleans, Louisiana. (one page).

S. Nehrer et al., "Chondrocyte-Seeded Type I and Type II Collagen Implants Investigated In Vitro", Fifth World Biomaterials Congress, May 29-Jun. 2, 1996, Toronto, CA. (one page).

S. Nehrer et al., "Autologous Chondrocyte-Seeded Type I and II Collagen Matrices Implanted in a Chondral Defect in a Canine Model", 44th Annual Meeting, Orthopaedic Research Society, Mar. 16-19, 1998, New Orleans, Louisiana. (one page).

S. Nehrer et al., "Chondrocyte-Seeded Type I and Type II Collagen Matrices Implanted in a Chondral Defect in a Canine Model", 7th Conference European Orthopaedic Research Society, Barcelona, 1997. (one page).

S Nehrer et al , Characteristics of Articular Chondrocytes Seeded in Collagen Matrices in Vitro Tissue Engineering 1998, op 175-183 vol. 4(2).

S. Nehrer et al., "Matrix Collagen Type and Pore Size Influence Behaviour of Seeded Canine Chondrocytes", Biomaterials 18, (1997), pp. 769-776.

Donna Schulz-Torres et al., "Tendon Cell Contraction of Collagen-Gag Matrices In Vitro: Effect of Cross-Linking", Soc. for Biomaterials, Apr. 28-May 2, 1999, Providence, R.I. (one page).

T.O. Schneider et al., "Expression of α-Smooth Muscle Actin in Canine Intervertebral Disc Cells In Situ and in Collagen-Gag Matrices In Vitro", J. Orthopaedic Research In press, pp. 1-22.

S. Nehrer et al., "Canine Chondrocytes Seeded in Type I and Type II Collagen Implants Investigated In Vitro", J. Biomed. Mater. Res. (Appl. Biomater.), 1997, pp. 95-104, vol. 38, John Wiley & Sons, Inc.

S.M. Mueller et al., "α-Smooth Muscle Actin and Contractile Behavior of Bovine Meniscus Cells Seeded in Type I and Type II Collagen-Gag Matrices", J. Biomed. Mat. Res., 1999, pp. 1-10, vol. 45, John Wiley & Sons, Inc.

Genzyme Tissue Repair, "Carticel™(autologous cultured chondrocytes), Engineering a Better Repair", Genzyme Tissue Repair, 64 Sidney Street, Cambridge, MA 02139-4136, Sep. 1997, brochure. (8 pages).

D. Mutter et al., "Biomaterial Supports for Colonic Wall Defect Healing", Biomaterials 17, 1996, pp. 1411-1415.

* cited by examiner

RESORBABLE EXTRACELLULAR MATRIX FOR RECONSTRUCTION OF CARTILAGE

CROSS-REFERENCE TO RELATED APPLICATIONS

The present application is a continuation-in-part of U.S. Ser. No. 09/986,75 7, filed Nov. 9, 2001, now U.S. Pat. No. 6,676,969, which is a continuation of U.S. Ser. No. 08/894, 517, filed Nov. 10, 1997, now U.S. Pat. No. 6,326,029, which is a §371 of PCT/GB96/00399, filed Feb. 22, 1996.

FIELD OF THE INVENTION

The present invention relates to the field of reconstruction of cartilage tissue.

DESCRIPTION OF THE BACKGROUND ART

Joint injuries often result in damage to the cartilage which lies between the joints. For example, knee injuries often result in meniscus damage.

Similarly, back injuries often involve damage to one or more vertebral discs.

There remains a need in the art for materials and methods for promoting regeneration of damaged cartilage.

SUMMARY OF THE INVENTION

In accordance with the present invention, a resorbable extracellular matrix for reconstruction of cartilage tissue comprises a purified collagen II derived from natural cartilage tissue. The matrix may be utilized as a scaffold implant for meniscal cartilage regeneration or for vertebral disc regeneration.

DETAILED DESCRIPTION OF THE INVENTION

Collagen occurs in a number of forms in the animal body and different tissues contain different proportions of the respective types. Thus, whereas bone collagen comprises predominantly collagen I and III, cartilage comprises predominantly collagen II together with small quantitites of collagen VI, IX, X, XI and XIII. Such material differs significantly from collage sponge material used in medicine and in cosmetics which, being derived from skin and tendons is mostly made up of collagen I and/or III.

According to one aspect of the present invention, therefore, there is provided a resorbable extracellular matrix for reconstruction of cartilage tissue comprising predominantly fibres of collagen II.

Figure 1:
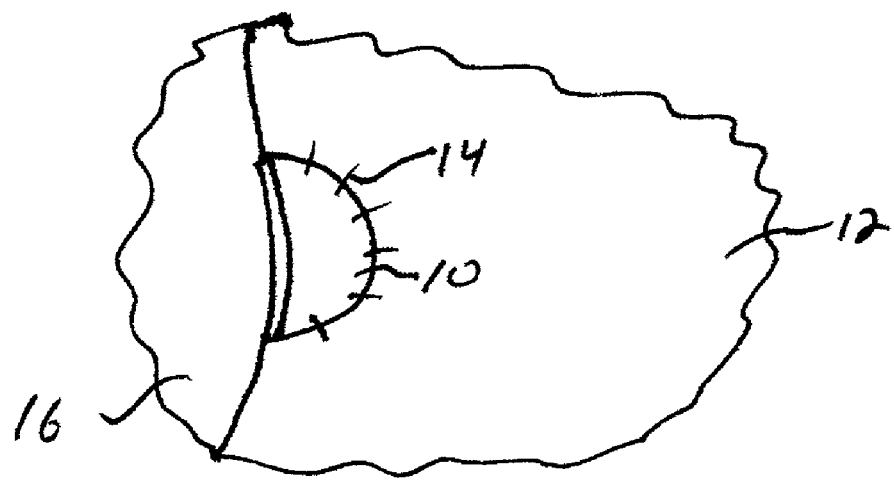
FIG. 1 is an elevational view, partly schematic, showing a meniscal scaffold implant in accordance with the invention.

FIG. 1 shows a meniscal scaffold implant 10 inserted into a defect in meniscus 12, fixed in place by sutures 14 over underlying bone material 16.

Figure 2:
FIG. 2 is an elevational view, partly schematic, showing a vertebral disc scaffold implant in accordance with the present invention.

FIG. 2 shows a vertebral disc scaffold implant 18 inserted into a defect into a vertebral disc 20, and fixed in place by sutures 22, or alternatively glueing with adhesive such as fibrin glue.

As indicated above, a collagen II matrix according to the invention may contain minor quantitites of collagen VI, IX, X, XI and XIII. The matrix according to the invention may also contain a hydrogel-like material, for example comprising glycosaminoglycans such as chondroitin sulphate, keratan sulphate, dermatan sulphate and hyaluronic acid, which provides a natural medium in which chondrocytes can become embedded and grow. The matrix according to the invention preferably contains 0.1 to 40% by weight of glycosaminoglycan, for example 1–15%, e.g., about 2–3 by weight, most preferably about 2.5% by weight.

The matrix according to the invention may either comprise natural cartilage material which has been subjected to defatting and other treatment, leaving the collagen II material together with glycosaminoglycans, or alternatively fibres of purified collagen II may be mixed with glycosaminoglycans and/or any other additives. Such additional additives may, for example, include chondronectin or anchorin II to assist attachment of the chondrocytes to the collagen II fibres and growth factors such as cartilage inducing factor (CIF), insulin-like growth factor (IGF) and transforming growth factor $\beta$ (TGF$\beta$).

The matrix is capable of acting as a medium for the ingrowth of native chondrocytes thereby effecting regeneration of cartilage tissue. However, to further aid in regenerating cartilage tissue the matrix may be impregnated with chondrocytes either prior to or following implantation in vivo. While the matrix may be impregnated with chondrocytes immediately prior to implantation, e.g. by injection, it is expected that in general the chondrocytes will be introduced into the matrix by direct injection of a suspension of chondrocytes following implantation. In this way, chondrocytes present in the matrix are able to effect regeneration of cartilage, and possibly new bone.

Chondrocytes for use in the invention may be obtained from cell sources which include allogenic or autogenic cells isolated-from articular cartilage, periosteum and perichondrium, and mesenchymal (stromal) stem cells from bone marrow. Since allogenic cells carry the potential for immune response and infectious complications, it is preferable to isolate the chondrocytes from autogenic cells, especially from autogenic articular cartilage. Techniques for harvesting cells are known and include enzymatic digestion or outgrowth culture. The harvested cells are then expanded in cell culture prior to reintroduction to the body. In general, at least $10^6$, preferably at least $10^7$ cells should be impregnated into the matrix to provide for optimal regeneration of cartilage tissue.

In general, it is desirable for the matrix according to the invention to contain glycosaminoglycans (GAGs) such as hyaluronic acid, chondroitin 6-sulphate, keratin sulphate, dermatan sulphate, etc., which serve to provide a natural medium in which chondrocytes can become embedded and grow. While it is possible to incorporate into the collagen matrix glycosaminoglycans from different sources which do not necessarily have the same composition, molecular weight and physiological properties as those from cartilage, preferred glycosaminoglycans are those extracted from cartilage itself.

In native collagen tissues GAGs occur, at least in part, as a component of proteoglycans (PGs). The use of GAGs in the form of PGs is undesirable in view of potential immunological problems which can be caused by the protein content of the PGs. Preferably, the matrix is thus substantially free from any proteoglycans. Conveniently, this may be achieved by preparing the matrix from a mixture of a purified telopeptide-free collagen material and glycosaminoglycans.

Other additives which may also be present in the matrix include, for example, chondronectin, laminin, fibronectin, calcium alginate or anchorin II to assist attachment of the chondrocytes to the collagen II fibers, bone and cartilage cell growth-promoting hormones, and growth factors such as cartilage inducing factor (CIP), insulin-like growth factor (IGF), transforming growth factor β (TGFβ) present as homodimers or heterodimers, osteogenic protein-1 (OP-1) and bone morphogenetic factors (BMPs) such as native or recombinant human BMP-2, BMP-3 (osteogenin), BMP-4, BMP-7, BMP-8, bFGF, CDMP or other skeletal matrix molecules, as well as signaling peptides such as transforming growth factor-β (TGFβ, TGF-β1), vascular endothelial growth factor (EGF/VEGF), insulin-like growth factor (IGF/IGF-1), parathyroid hormone related protein (PTHrP) and platelet derived growth factor (PDGF). Nucleic acid sequences coding for the above, or which are capable of inducing or promoting in vivo production of the above, may be incorporated into the collagen matrix material of the present invention.

The product used in the invention also may act as a carrier for stem cells committed to a particular line of differentiation such as articular cartilage or bone. Such stem cells may be grown in vitro to increase their numbers, and applied to the repair sites in the carrier matrices with or without growth factors. Examples include mesenchymal stem cells and bone marrow stromal cells. Nucleic acid sequences coding for the above, or which are capable of inducing or promoting in vivo production of the above, may be incorporated into the collagen matrix material of the present invention.

BMP-2 affects the two pathways of bone formation independently—the direct formation of bone as well as the formation of cartilage which is then removed and replaced by bone. Composites of BMPs and collagen including bone matrix obtained by extraction from cortical bone from various sources or demineralized bone matrix comprise about 90% collagen and about 10% non-collagenous proteins (NCP) for BMP activity or for BMP/NCP induced chondrogenesis. Bone matrix-insoluble collagenous matrix and laminin or fibronectin act as carriers for BMPs. In general, the matrix may contain from about 100 μg to about 5 mg of growth factors. Nucleic acid sequences coding for the above, or which are capable of inducing or promoting in vivo production of the above, may be incorporated into the collagen matrix material of the present invention.

A matrix material for use in accordance with the present invention may also be charged with parathyroid hormone (PTH), a polypeptide involved in regulation of calcium in the body. Nucleic acid sequences coding for the above, or which are capable of inducing or promoting in viva production of the above, may be incorporated into the collagen matrix material of the present invention.

As noted above, the present invention may comprise a gene or nucleic acid-supplemented collagen matrix with cell growth-promoting genetic material or DNA incorporated therein. The collagen matrix material may provide for prolonged release of the cell growth-promoting genetic material. Upon release from the matrix into the body, the genetic material may transform cells in the body so as to promote cell growth and healing.

The present invention may also provide a collagen matrix material charged with a cell growth-promoting nucleic acid sequence, preferably an isolated or purified nucleic acid sequence. The sequence can be a DNA sequence or an RNA sequence. In particularly preferred embodiments, the collagen matrix material is charged with an isolated gene sequence, most preferably of DNA.

A nucleic acid sequence for use in accordance with the present invention may promote cartilage cell growth, bone cell growth, or both.

Purified therapeutic nucleic acid sequences for use in accordance with the present invention may be derived from any suitable source, and may be charged to the collagen matrix material so as to promote cell growth. In accordance with one embodiment, a retroviral vector, or any other suitable gene-carrying and gene-introducing mechanism, is utilized. For example, a retroviral vector may be utilized for stably introducing human bone morphogenic protein 7 (BMP-7) cDNA into mesenchymal stem cells.

Gene therapy in accordance with the present invention involves the delivery of therapeutic genes or other genetic material into cells and tissues.

As will be further discussed below, a scaffold implant of the matrix of the invention may be prepared by forming an aqueous collagen slurry, optional partial dehydration of the slurry, molding the slurry to the desired shape, drying of the slurry, partial cross-linking of the collagen fibers by chemical, ultraviolet (UV) radiation or hydrothermal cross-linking, and sterilizing the implant material. Alternatively, cross-linking, such as chemical cross-linking, can be effected after preparation of the slurry and prior to molding.

In preferred embodiments, the molded material is dried by freeze-drying so as to achieve a pore size within the range of about 0.1–500 μm. A preferred pore size for a scaffold implant in accordance with the invention is within the range of about 50–400 μm, most preferably within the range of about 70–120 μm.

The density of the matrix after freeze-drying preferably is within the range of about 0.1–0.3 g/m$^3$, preferably about 0.18–0.22 g/m$^3$, most preferably about 0.2g/m$^3$.

The collagen material may be cross-linked before or after the freeze-drying step to stabilize the matrix. This also serves to increase the mechanical stability of the matrix and to reduce its rate of resorption by the body. Ideally, the degree of cross-linking should be such that the rate of degradation of the matrix matches the rate of tissue regeneration. Physically, cross-linking may be carried out by heating, but this must be effected carefully to avoid undesired loss of resorbability. Heating to temperatures of 100–120° C. for a period of from about 30 minutes to about 5 hours is preferable. More preferably, cross-linking may be effected by UV irradiation using a UV lamp, e.g., for a period of up to 8 hours.

As noted above, the collagen material advantageously contains glycosaminoglycans (GAGs). The latter actually reacts with the collagen to effect some cross-linking and produces an insoluble product. If necessary, further cross-linking can be effected by heating the material, by UV irradiation, or by further chemical cross-linking as discussed above. The reaction between the glycosaminoglycans and the collagen can be effected at ambient temperatures at a pH in the range 2.5–3.5. The material may be subjected to freezing and freeze-drying immediately after such treatment.

For example, GAGs such as chondroitin sulphate (CS) may be covalently attached to the collagen matrix using 1-ethyl-3-(3-dimethyl aminopropyl) carbodiimide (EDC) and N-hydroxysuccinimide (NHS) utilizing known methods. EDC/NHS crosslinking may be utilized for immobilizing GAGs with collagen matrices, which may include dermatan sulphate, heparin, heparan sulphate, and hyaluronic acid, as well as CS as indicated above.

Slurry formation may be effected by raising the pH of the collagen mass. In this procedure, the mass is cooled to about 4° C. and the pH value slowly raised by addition of cold aqueous NaOH at 4° C. up to a pH value about 6.5–7.5. Subsequently, the mass is held at ambient temperature for about 15–25 hours. In this time, the slurry is formed and after slurry formation, the mass can be molded, frozen and freeze-dried.

A still further alternative is to neutralize the collagen mass to a pH value about 6.8–7.4, subsequent to removal of air. The mixture is placed in the mold and incubated for about 15–20 hours at 37° C. A fine slurry develops which can subsequently be frozen and freeze-dried.

After molding the slurry, the material is frozen. In order to obtain a reproducible pore size, the freezing must be carefully controlled and the rate and time of freezing, the pH value and the particle size must be accurately controlled.

The matrix is then freeze-dried and subsequently heated to about 110–130° C. In this way, some cross-linking is effected. Subsequently, the freeze-dried matrix may be adjusted to the required thickness. The matrix is then sterilized, for example by gamma-irradiation or with ethyleneoxide. Sterilization by strong irradiation e.g. with $^{60}CO$ in doses of 25 kGy may deactivate the BMPs. In such circumstances, the sterile matrix may be impregnated with BMPs in sterile saline prior to implantation.

The thickness of a scaffold implant in accordance with the present invention may be within the range of about 0.2–2 cm, preferably about 0.3–1.5 cm, more preferably about 0.4–1 cm, and most preferably about 0.5–0.8 cm.

When cross-linking is effected utilizing chemical agents, various aldehydes such as hyaluronate polyaldehyde, formaldehyde or glyoxal may be used. Suitable chemical cross-linking agents include hyaluronate polyaldehyde, hexaethylene di-isocyanate, di-ethyl-3-(3-dimethyl aminopropyl) carbodimide (EDC), and N-hydroxy succinimide (NHS) or a mixture of EDC and NHS.

There exists a wide range of glycosaminoglycans and proteoglycans which have different and sometimes undesirable properties. Thus, although it is possible to incorporate into the collagen matrix glycosaminoglycans from different sources which do not have the same composition, molecular weight and physiological properties as glycosaminoglycans from cartilage, it is particularly preferred to use glycosaminoglycans from cartilage itself.

As noted above, it is desirable to subject the collagen matrix to some degree of cross-linking in order to restrict the extent of swelling when the matrix comes in contact with aqueous fluids, while retaining the ability of the matrix to be resorbed. Such swelling leads to loss of strength and shape. The collagen matrix according to the invention may advantageously be manufactured by subjecting cartilage tissue to defatting followed by treatment with a base whereby proteoglycans and glycosaminoglycans are removed.

The cartilage material will normally be that from readily available animal sources such as cattle, sheep or pigs. The preferred material is hyaline cartilage from pigs. This contains the right type of collagen and glycosaminoglycan in desirable proportions and is available in suitably large quantities.

The cartilage is preferably frozen after slaughter and subjected to size reduction, for example to a particle diameter of about 8 mm. Before size reduction, the cartilage is preferably soaked in water and mechanically separated from flesh, bone and other unwanted materials.

The particulate cartilage is then preferably subjected to dewatering by treatment with a water miscible organic solvent such as acetone, which also serves to remove some fat. The dewatering shrinks the collagen fibres and separates them from each other so that the subsequent defatting step is optimised. The material is then subjected to defatting with a fat-solvent such as a hydrocarbon e.g., hexane, or a halogenated hydrocarbon.

After defatting, the material is thoroughly washed and this is continued until as much water has been taken up as was present originally. By this procedure, the material is optimised for the base-treatment which follows.

The base-treatment may be effected with a strong alkali, for example an alkali metal hydroxide, e.g., sodium hydroxide, for example at a concentration of 1–8% by weight. The treatment time, which will vary according to the raw material and alkali concentration, is generally 10–48 hours. The treatment temperature will generally be below 20° C. The pH value is normally in the range 12–14. The above conditions are those which are optimal for treatment with NaOH. Treatment with other bases may require slightly modified conditions.

The base-treatment has the following effects:

Small quantities of residual fat are saponified. The non-collagen, alkali soluble proteins are denatured, destroyed, dissolved and eliminated.

The amide groups in the collagen are saponified, thereby changing the electric charge and the isoelectric point of the collagen.

Bacteria, prions and viruses are inactivated and the collagen is thus sterilised.

It has been found that by this treatment, proteoglycans undergo a useful modification which can be characterised as follows:

the covalent binding of glycosaminoglycans to the core protein in proteoglycans is cleaved. In this way the glycosaminoglycans can be liberated from the protein of the proteoglycans. This is termed β-elimination.

By the base-treatment, the core protein is split into small peptides which may be removed from the reaction mixture by dialysis or ultra filtration.

Due to the strong negative charge, the glycosaminoglycans form water soluble salts which can partially washed from the collagen. These are, however, uncleaved or only slightly cleaved by the base-treatment and can be separated from peptides by dialysis. A part of the glycosaminoglycan (about 3% by weight of the collagen) is bound to the collagen.

Purified glycosaminoglycans may be obtained by dialysis or ultrafiltration of the extract arising from the base-treatment step.

According to the procedure of the present invention, enzymatic treatment is, in general, not used, in view of the variety of different substances present. However, further steps include treating the material with an organic or inorganic acid, such as hydrochloric acid. This has the following effect:

Unwanted acid sensitive materials are removed; The fibre structure is loosened.

Subsequently, the material is washed, generally until the pH value of the material is between 2.5 and 4.0. The pH value of the material is preferably controlled accurately. The pH value of the material should be uniform across the cross-section of the cartilage.

After the acid treatment, the cartilage is in a water-swelled condition. The material is then subjected to mechanical size-reduction, for example using a colloid mill. The concentration of the collagen in the aqueous medium is then about 2.5–3.5% by weight. The pH value of this mixture should be somewhat acid, for example 3.5–4.5.

At this point, one or more glycosaminoglycans may be added to the purified collagen mass, for example in the range 0.1–40% preferably 1 to 15%, of the weight of collagen.

The glycosaminoglycans added to the collagen preferably are extracted from the natural cartilage, as indicated above. The matrix will then contain, besides collagen II, the glycosaminoglycans hyaluronic acid, chondroitin sulphate and keratan sulphate. The chondroitin sulphate and keratan sulphate are covalently bonded to the core protein while hyaluronic acid is, indeed, bound to the proteoglycan but not covalently.

By the action of the base, the bonding to the core protein is cleaved and the glycosaminoglycan is freed from the protein. Additionally, the core protein is cleaved to small peptides which are readily removed by dialysis or ultrafiltration. It is important that the core protein is removed, since this may be immunologically active. The removal of the core protein is thus an important part of the process of the present invention.

The recovery of the glycosaminoglycans from the base extract may be effected as follows:

The medium is neutralised to a pH value in the range 6–8.

The non-collagen proteins care removed by treatment with an adsorbent such as kaolin.

Ultrafiltration of the liquid is effected, using a membrane which permits the passage of molecules of weight less than 10000 daltons.

Concentration of the liquid is effected to a solids content of about 2–5 weight percent.

After admixture of the glycosaminoglycan with the collagen II, the material is homogenised still further in a colloid mill and the solid content is adjusted to 1.5–2.5 weight percent. This mass can then serve for the production of two types of product, namely a sponge or a collagen sheet.

For the production of a sponge, the mass resulting from homogenisation is frozen. The freezing must be precisely controlled, whereby the freezing time, pH value and particle size are exactly maintained in order to provide a reproducible pore size. The frozen product is then freeze-dried. After freeze-drying, the sponge is warmed to 120–140° C. for at least 2 hours. In this way, the material is stabilised by light cross-linking. After the freeze-drying the material is cut to a desired thickness, stamped to the required shape, sterilised and packed.

Because the use of sponges is limited for use in some fields due to insufficient strength, the collagen matrix according to the invention can advantageously be used for the production of collagen sheets, which are suitable for use in a wide range of medical indications.

For the production of collagen sheets, the concentration of purified II collagen fibres in the liquid suspension should be in the range 0.2–3 weight percent, advantageously 0.5–2 weight percent. Air is preferably removed.

A gel is then formed as an intermediate step. The production of the collagen gel can be effected by various techniques known for gel formation.

The gel is then dried, normally on a plate. In this way, not only is water removed but insoluble collagen-glucosaminoglycan products are formed which are very beneficial for the growth of cells.

For either the above products, the matrix according to the invention can be supplemented with active substances. Thus any physiologically active substance which is water soluble or water dispersible can be used. Thus, the matrix may advantageously contain medicinal substances such as antibacterials, e.g., taurolidine, taurultam, or antibiotics such as tetracyclines and gentamycins.

The invention also provides the use of a matrix according to the invention in guided regeneration of cartilage tissue.

A method in accordance with one embodiment of the invention comprises, removing damaged cartilage tissue located adjacent to or between bone material, inserting a scaffold implant comprising collagen II material which has been sized to fit the area of damaged cartilage, and fixing the scaffold implant in the area of damaged cartilage by any suitable means such as adhesive or suturing the scaffold implant to adjacent cartilage material.

The following examples are given by way of illustration only.

EXAMPLE 1

Frozen cartilage from freshly slaughtered pigs was steeped in cold water, thoroughly washed through and mechanically purified from flesh residues, bones and hard pieces. Subsequently, the material was washed for 30 minutes under flowing water.

Subsequently, the material was ground three times in a homogenizer. The optical particle size at the end of size reduction was about 8 mm.

The cartilage pieces were dewatered by washing 4 times with acetone, each time for 8 hours. The cartilage was then defatted by extraction 4 times with n-hexane. Each treatment lasted at least 8 hours. The ratio of hexane to cartilage was 1:10.

After defatting, the cartilage was swelled in drinking water. The ratio of water:material was 10:1. The treatment time was 24 hours.

The material was then treated with NaOH (5% by weight) whereby the ratio of cartilage to liquid was 1:4 and the treatment time was 32 hours. During the treatment, the pieces of cartilage were well stirred. Subsequently, the alkali was washed from the cartilage. The original pH of 14 was thereby reduced to 9–11. The dissolved impurities were washed out and separated from the cartilage. The liquid resulting from the alkaline treatment was collected for the recovery of glycosaminoglycan.

The collagen material was then treated with strong HCl (about 3% by weight) initially at a pH value under 1.0. The treatment time was 4–6 hours.

Subsequently, the material was washed with cold water long enough for the pH value to rise to 3–3.5.

All impurities were removed and the product was a salt-free collagen mass, suitable for-production of a sponge or other collagen material. For that purpose, the cartilage mass may be, according to the intended result, degassed, frozen and freeze-dried.

EXAMPLE 2

The extract resulting from alkaline treatment in Example 1 contained glycosaminoglycan, alkali, denatured proteins and salts. The extract was firstly neutralised with HCl, the pH value after neutralisation being 6. The extract was then treated with a filter aid, namely kieselguhr, which had the effect of removing the denatured proteins. 0.5 weight percent of kieselguhr was introduced into the extract and removed by filtration together with the denatured protein.

The supernatant was then submitted to ultrafiltration using a membrane having a molecular weight cut off at about 10000 daltons. In this way, salts were removed to leave purified glycosaminoglycan.

The glycosaminoglycan solution so obtained was admixed with collagen material from above to provide a collagen II matrix containing glycosaminoglycan.

EXAMPLE 3

(1) Determination of Hexosamine and Amino Acid Residues in Collagen Sponges and Fleeces Each sample, exactly weighed (about 10 mg) was hydrolised in 10 ml of 3M or 6M HCl at 1.05° C. for 15 or 20 hours under purified nitrogen in a sealed tube. After cooling the tube in a refrigerator and opening the tube, the contents were transferred to a 25 ml long neck flask and dried at 40° C. in a vacuum-rotation dryer (Rotavapor RE120, Büchi, Switzerland) under water jet vacuum. After dissolving the residue in 5 ml water, the residue was again dried under water jet vacuum. Subsequently, the residue was taken up in 5 ml loading buffer (0.2M relative to Na+) at pH 2.2. For determination of the glucosamine and galactosamine values, after previous dilution of an aliquot with loading buffer (1+10) 150 µl of the sample hydrolysed in 3M HCl was injected into the cartouche of an amino acid analyser (AlphaPlus, type 4151, Pharmacia-LKB, Freiburg) and evaluated by comparison with a standard with the help of a computer (Shimadzu, Duesseldorf). The same procedure was effected with the sample hydrolised in 6M HCl, wherein 50 µl were injected in a further test cartouche. The double hydrolysis in 3M and 6M HCl is necessary for optimisation of the hexosamine and amino acid analysis since the maximal values for hexosamine and also tyrosine are only obtained after hydrolysis in 3M HCl while maximal values are only obtained for valine, isoleucine and leucine after hydrolysis in 6M HCl.

(2) Determination of Native Collagen Content in Collagen Sponges and Fleeces

25–30 mg (exactly weighed out) of sample were introduced into 30 ml 0.1M sodium hydrogen carbonate solution (pA, Merck, Darmstadt) pH 8.2 to which 1.5 ml of a 6 mg/ml trypsin solution (lyophilised preparation from bovine pancreas, Boehringer, Mannheim) and incubated for 8 hours at 23±1° C. in a shaking water bath (Julabo SWI, Seelbach). After cooling the sample in a cold room to 4° C., it was centrifuged at 4° C. in a 60 Ti-Rotor (Beckman, Munich) at 32000 RpM for 30 minutes. The residue was filtered in a stirred ultra filtration cell (Mod 8010, Amicon, Witten) through a Diaflow-Filter PM 10 (Amicon, Witten) of diameter 25 mm and 1 ml of the filtrate was hydrolysed in 6M HCl for 20 hours at 105° C. The further working up and analysis of the hydrolysate is identical with that described under (1) above with the exception that the further uptake of the sample after twice evaporating to dryness, was in 150 µl loading buffer, whereby 150 µl was injected into the test cartouche of the amino acid analyser. The hydroxyproline value obtained after the amino acid analysis (in µmol/g starting substance), represents the part of the degradable collagen in the sample. When the hydroxyproline value of a parallel hydrolysis (6M HCl and analysed sample (see (1) above) which represents the total collagen content, is compared with the hydroxyproline value, the percentage proportion of the "native", that is trypsin non-degradable collagen is indicated.

The results are shown in the following table.

TABLE

|  | µmol/g | mol/1000 mol |
| --- | --- | --- |
| Hydroxyproline | 795.4 | 97 |
| Aspartic acid | 381.7 | 47 |
| Threonine | 190.1 | 23 |
| Serine | 257.0 | 31 |
| Glutamic acid | 691.3 | 84 |
| Proline | 913.2 | 112 |
| Glycine | 2614.6 | 320 |
| Alanine | 864.9 | 106 |
| Cysteine/2 | 11.5 | 2 |
| Valine | 195.7 | 24 |
| Methionine | 62.7 | 8 |
| Isoleucine | 92.8 | 11 |
| Leucine | 229.9 | 28 |
| Tyrosine | 27.0 | 3 |
| Phenylalanine | 119.9 | 15 |
| Histidine | 39.8 | 5 |
| Hydroxylysine | 126.4 | 15 |
| Lysine | 173.5 | 21 |
| Arginine | 395.5 | 48 |
| Total | 8182.9 | 1000 |
| Glucosamine | 9.68 | 1.18 |
| Galactosamine | 46.30 | 5.66 |
| Total Hydroxyproline | 795.4 µmol/g |  |
| Trypsin-degradable hydroxyproline | 36.9 µmol/g |  |
| "Native" collagen content | 95.4% |  |

The invention claimed is:

1. A resorbable extracellular matrix for reconstruction of cartilage tissue, said matrix consisting essentially of a purified collagen II derived from natural cartilage tissue from which non-collagen proteins have been removed, wherein said natural cartilage tissue is subjected to defatting, wherein said matrix consists essentially of fibres of native collagen II which are physiologically acceptable for implant into a mammalian body, said matrix having a pore size within a range of about 50–400 µm.

2. A resorbable extracellular matrix as claimed in claim 1 having a pore size within a range of about 70–120 µm.

3. A resorbable extracellular matrix as claimed in claim 1 containing at least one glycosaminoglycan (GAG) comprising about 1–15% by weight of said matrix.

4. A resorbable extracellular matrix as claimed in claim 3 wherein said at least GAG comprises about 2–3% by weight of said matrix.

5. A resorbable extracellular matrix claimed in claim 1 having a density of about 0.18–0.22 g/m$^3$.

6. A resorbable extracellular matrix as claimed in claim 1 wherein said matrix includes a material selected from the group consisting of at least one glycosaminoglycan (GAG), chondronectin, anchorin II, cartilage inducing factor (CIF), insulin-like growth factor (IGF), transforming growth factor β(TGFβ) and a mixture thereof.

7. The resorbable extracellular matrix of claim 1 wherein said GAG is selected from the group consisting of chondroitin sulphate, keratan sulphate, dermatan sulphate, hyaluronic acid, and a mixture thereof.

8. A resorbable extracellular matrix as claimed in claim 1 which is derived from hyaline cartilage from pig.

9. A scaffold implant for promoting cartilage regeneration comprising the matrix of claim 1, said implant having a thickness of about 0.2–2 cm.

10. The scaffold implant of claim 9 having a thickness of about 0.4–1 cm.

11. The scaffold implant of claim 9, wherein said matrix is a carrier of a material selected from the group consisting of mesenchymal stem cells and a cartilage cell growth-promoting nucleic acid sequence.

* * * * *